US007244568B2

(12) United States Patent
Goldsborough (10) Patent No.: US 7,244,568 B2
(45) Date of Patent: *Jul. 17, 2007

(54) ISOLATION OF NUCLEIC ACID

(75) Inventor: Andrew Simon Goldsborough, St. Gely du Fesc (FR)

(73) Assignee: Cyclops Genome Sciences Limited, Cambridge (GB)

( * ) Notice: Subject to any disclaimer, the term of this patent is extended or adjusted under 35 U.S.C. 154(b) by 359 days.

This patent is subject to a terminal disclaimer.

(21) Appl. No.: 10/820,423

(22) Filed: Apr. 8, 2004

(65) Prior Publication Data

US 2005/0074753 A1    Apr. 7, 2005

Related U.S. Application Data

(63) Continuation of application No. 10/031,636, filed as application No. PCT/GB00/01684 on May 2, 2000, now Pat. No. 6,794,140.

(30) Foreign Application Priority Data

| Apr. 30, 1999 | (GB) | ................................. | 9910154.5 |
| Apr. 30, 1999 | (GB) | ................................. | 9910156.0 |
| Apr. 30, 1999 | (GB) | ................................. | 9910157.8 |
| Apr. 30, 1999 | (GB) | ................................. | 9910158.6 |

(51) Int. Cl.
*C12Q 1/68* (2006.01)
*C12P 19/34* (2006.01)
*C07H 21/04* (2006.01)

(52) U.S. Cl. ...................... 435/6; 435/91.2; 536/25.32
(58) Field of Classification Search .................... 435/6, 435/91.2; 536/25.32
See application file for complete search history.

(56) References Cited

U.S. PATENT DOCUMENTS

| 5,426,180 | A | 6/1995 | Kool |
| 5,660,985 | A | 8/1997 | Kirschenheuter et al. |
| 5,681,726 | A | 10/1997 | Huse et al. |
| 5,707,796 | A | 1/1998 | Gold et al. |
| 5,783,425 | A | 7/1998 | Dudycz |
| 5,859,221 | A | 1/1999 | Cook et al. |
| 5,872,232 | A | 2/1999 | Cook et al. |
| 6,794,140 | B1 | 9/2004 | Goldsborough |
| 6,867,290 | B2 | 3/2005 | Goldsborough |
| 2005/0272679 | A1 | 12/2005 | Goldsborough |
| 2006/0147918 | A1 | 7/2006 | Goldsborough |

FOREIGN PATENT DOCUMENTS

| WO | 92/03568 | 3/1992 |
| WO | 98/13526 | 4/1998 |
| WO | 99/14346 | 3/1999 |
| WO | 99/36517 | 7/1999 |
| WO | 99/55857 | 11/1999 |
| WO | WO 2000/06605 | 11/2000 |
| WO | WO 2000/066605 | 11/2000 |
| WO | WO 2000/075302 | 12/2000 |
| WO | WO 2000/075306 | 12/2000 |
| WO | WO 2001/094626 | 12/2001 |
| WO | WO 2005/012522 | 2/2005 |

OTHER PUBLICATIONS

U.S. Appl. No. 10/565,694, filed Jan. 23, 2006, claims only.
Heidenrich, Olaf et al., "Chemically Modified RNA: Approaches and Applications", The FASEB Journal, Jan. 1993, vol. 7.
Heidenrich, Olaf et al., "High Activity and Stability of Hammerhead Ribozymes Containing 2'-Modified Pyrimidine Nucleosides and Phosphorothioates", The Journal of Biological Chemistry, vol. 269, No. 3, Jan. 21, pp. 2131-2138, 1994.
Aurup, Helle et al., "Translation of 2'-Modified mRNA in vitro and in vivo", Nucleic Acids Research, 1994, vol. 22, No. 23, pp. 4963-4968.
Xin, Wei et al., "Treatment of Duck Hepatitis B Virus by Antisense Poly-2'-O-(2,4-Dinitrophenyl)-Oligoribonucleotides", Bioenergetics Laboratory, Natural Science Center, State University of NY, Buffalo, Jul. 1998.
Iribarren, Adolfo M. et al., "2'-0-Alkyl Oligoribonucleotides as Antisense Probes", Proc. Natl. Acad. Sci., vol. 87, pp. 7747-7751, Oct. 1990.
Inoue, Hideo et al, "Synthesis and Hybridization Studies on Two Complementary Nona(2'-0-methyl) Ribonucleotides", Faculty of Pharmaceutical Sciences, Hokkaido University, Sapporo 060, Japan, Jun. 1987.
Scherr, Michaela et al., "Synthesis and Properties of Hammerhead Ribozymes Stabilized Against Nucleases by Different 2'-Modifications: Methoxyethoxy-, Fluoro- and Amino Groups", Bioorganic & Medicinal Chemistry Letters, vol. 7, No. 13, pp. 1791-1796, 1997.
Lewis "Kits take the trickiness out of RNA isolation, purification" The Scientist 11(7):16 Mar. 31, 1997.
Ovodov, S.Y., "mRNA acetylated at 2'-OH-groups of ribose residues is functionally active in the cell-free translation system from wheat embryos", FEBS 270(1,2):111-114 (1990).
Pagratis, N.C. et al. "Potent 2'-amino-, and 2'-flouro-2'-deoxyribonucleotide RNA inhibitors of keratinocyte growth factor", Nature Biotechnology 15(1): 68-73 (1997).
Sproat, B.S., "Chemistry and applications of oligonucleotide analogues", Journal of Biotechnology 41:221-238 (1995).

*Primary Examiner*—Kenneth R. Horlick
*Assistant Examiner*—Joyce Tung
(74) *Attorney, Agent, or Firm*—Saliwanchik, Lloys & Saliwanchik (57) ABSTRACT

Provided is a preparative method for isolating RNA comprising an oligo-or polynucleotide from a sample, which method comprises: (a) treating the sample with a reactant capable of covalently modifying the 2'-OH position of the ribose rings of the RNA under conditions so that a proportion of the 2'-OH positions of the ribose rings bear a substituent; and (b) preparing isolated RNA therefrom by separating material containing the substituent from the sample on the basis of a property of the substituent.

3 Claims, 2 Drawing Sheets

ISOLATION OF NUCLEIC ACID

RELATED APPLICATIONS

This application is a continuation of U.S. patent application Ser. No. 10/031,636, filed Apr. 29, 2002, now U.S. Pat. No. 6,794,140, which is a 371 of PCT/GB00/01684, filed May 2, 2000, which claims priority to patent applications UNITED KINGDOM 9910154.5, filed Apr. 30, 1999, UNITED KINGDOM 9910157.8, filed Apr. 30, 1999, UNITED KINGDOM 9910156.0, filed Apr. 30, 1999, and UNITED KINGDOM 9910158.6, filed Apr. 30, 1999, each incorporated herein in their entireties.

FIELD OF THE INVENTION

The present invention relates to a method for isolating RNA from a sample and to a kit for use in such a method.

BACKGROUND OF THE INVENTION

The process by which RNA is separated from other molecules, in particular other cellular components such as proteins, carbohydrates, lipids and DNA is widely known and described in the literature. It is a key process in the understanding of gene function and structure and drug development. Furthermore nucleic acid based diagnostic procedures for detecting RNA viruses such as HCV and HIV absolutely require the viral genomic RNA to be isolated in an intact and relatively pure form. In order to separate RNA in an intact and pure form from other biological material it is necessary to rapidly inactivate all ribonucleases that are present and separate the RNA based on a biophysical property unique to the RNA. However, due to the similar physical characteristics of RNA and DNA, RNA preparations are frequently if not always contaminated with DNA, leading to major difficulties in the analysis of results.

Currently mRNA is separated from genomic DNA by using a method based on oligo (dT) interacting with the poly A tail (Aviv and Leder., Proc. Natl. Acad. Sci. USA. 69, 1408–1412 (1972). However, A-rich DNA sequences are co-purified with this method leading to mRNA contaminated with A-rich DNA. Alternatively, nucleases that are specific for either RNA or DNA can be employed. Such highly purified enzymes are costly to use and frequently require removal before the nucleic acid can be used. For example RNase free, DNase must be removed by phenol extraction or heat inactivation otherwise it will destroy for example PCR primers or other DNA based reagents in all post-nuclease reactions. Another method is to use a mixture of phenol, chloroform, isoamyl alcohol (50:49:1); whereby DNA preferentially partitions into the organic phase whilst RNA remains in the aqueous phase. This method at best still leaves a significant amount of DNA contaminating the RNA and hence is of limited practical use. Another method is the TRI REAGENT™ (Molecular Research Centre, Inc) that allows the simultaneous separation of DNA, RNA and proteins. However, it requires careful separation of different phases from each other and subsequent centrifugation steps whilst not assuring complete separation of DNA from the RNA due to the difficulty of pipetting small volumes of liquid without cross-contamination. Another method is anion exchange chromatography which can separate RNA from DNA but the expense and difficulty of setting up the column as well as the restriction to purifying only small nucleic acids precludes its use from the majority of laboratories. Numerous methods to purify RNA are described in general texts (Jones et al., (1994) in RNA Isolation and Analysis. Bios. Oxford., Sambrook et al., (1989) Molecular Cloning: A Laboratory Manual, CSH.).

SUMMARY OF THE INVENTION

The present invention provides a preparative method for isolating RNA comprising an oligo-or polynucleotide from a sample, which method comprises:

(a) treating the sample with a reactant capable of covalently modifying the 2'-OH position of the ribose rings of the RNA under conditions so that a proportion of the 2'-OH positions of the ribose rings bear a substituent; and (b) preparing isolated RNA therefrom by separating material containing the substituent from the sample on the basis of a property of the substituent.

The RNA may be mRNA, tRNA, rRNA, viral RNA, viroid RNA, synthetic RNA such as chemically synthesized or in vitro transcribed forms, or any other form of RNA, such as hnRNA. The RNA may be a mixture of different types of RNA and may be in single- or double-stranded form, linear or circular and contain internal regions of secondary and tertiary structure such as is commonly found in tRNA. According to the present invention an oligonucleotide generally has a sequence of up to about 80 bases and a polynucleotide generally has a sequence length of more than about 80, preferably more than about 100 bases. A preferred length for a polynucleotide is at least 1000 bases.

The mRNA may or may not have a cap and/or poly A tail. The RNA used in the present invention is preferably naturally-occurring. A naturally-occurring RNA according to the present invention typically comprises a nucleotide sequence which is found in nature and which has a structural function or generally encodes a polypeptide having biological activity, or such a nucleotide sequence which is modified, for example to alter in some way the biological activity of the polypeptide encoded thereby. Whilst the naturally-occurring RNA is preferably obtained by transcription from a suitable RNA or DNA template, itself usually naturally-occurring, in some cases the naturally-occurring RNA can be obtained synthetically. RNA according to the present invention does not encompass simple homopolynucleotides (poly A, poly U, poly G and poly C) which can be generated synthetically but are biologically non-functional.

The naturally occurring RNA can be derived from a biological material such as bacteria, viruses such as those causing infection in humans, animals or plants, viroids, or cells such as fungal, animal and plant cells.

An important aspect of this invention is modification of mRNA, rRNA and viral RNA since they are of major scientific and clinical interest and serve as a good example of the problems encountered when manipulating RNA. The invention further provides methods for obtaining intact full-length copies of mRNA, rRNA, viral RNA and other types of RNA isolated from cellular sources or extracellular fluids that demonstrate increased stability in conditions that would otherwise destroy a major fraction of the unmodified RNA.

Measuring the percentage modification of RNA:

Due to the polymeric nature of RNA, it is difficult to measure its molecular weight above 100 nucleotides using mass spectrometry because a large amount of RNA degradation occurs during the analytical process. However, RNA (tRNA) up to 142 nucleotides (Nordhoffet al., (1993) Nucleic Acids Res. 21:3347; Gruic-Sovulj et al., (1997) Nucleic Acids Res. 25:1859; Tolson and Nicholson (1998) Nucleic Acids Res. 26:446) and double stranded DNA up to 500 base-pairs (Bai et al., (1995) Rapid Comm. Mass Spectrom. 9:1172; Taranenko et al., (1998) Nucleic Acids Res. 26:2488; Ausdall and Marshall (1998) Anal. Biochem. 256:220) have been measured using MALDI mass spectrometry (for reviews see; Smith (1996) Nat. Biotech. 14:1084; Murray (1996) J. of Mass Spectrom. 31:1203. Phosphate (Schuette et al., (1995) J. Pharm. Biomed. Anal. 13:1195; Sinha et al., (1994) Nucleic Acids Res. 22:3119) and chemically modified oligonucleotides (Potier et al., (1994) Nucleic Acids Res. 22:3 895) have also been measured using mass spectrometry.

Although there is a molecular weight limitation to a few hundreds of nucleotides when using mass spectrometry, it provides a simple, automated means to accurately determine the exact molecular weight and therefore the percentage modification of a polynucleotide. Optimisation relies on a number of factors such as the type of mass spectrometry being carried out (electro-spray, MALDI-TOF etc), the method used to purify the modified RNA from the modification reaction, the size of the polynucleotide, the ionization matrix used, the method used to remove cations from the RNA, positive or negative ion mode and the voltage strength used (Fenn et al., 1989) Science 246:64). Capillary high performance liquid chromatography can be used prior to mass spectrometry of RNA because desalting and other purification steps are not required prior to ionization (Taniguchi and Hayashi (1998) Nucleic Acids Res. 26:1481).

To measure the molecular weight and hence the percentage modification of polynucleotides consisting of thousands of nucleotides requires a different approach. In certain situations where it is preferable to measure the percentage modification of the polynucleotide using more precise means a degradative step may be employed followed by an analytical process. It is expected that degradation of the modified polynucleotide using chemical or enzymatic means will, depending on the method used leave the 2'-OH modification attached to the ribose sugar allowing the amount of modification to be established by mass spectrometry or high performance liquid chromatography (HPLC). HPLC and gas chromatography analysis of nucleotides has been described (Gehrke and Patel (1977) J. Chromat. 130:103; Iwase et al., (1975) J. Chromat. 106:213; Kemp et al., (1982) J. Chromat. 241:325).

In order to establish the percentage of nucleotides that are modified, degradation of the polynucleotide should follow the modification reaction. Methods have been described for enzymatic cleavage methods employing ribonucleases RNase T1, RNase A, RNase U2, RNase PhyM, RNase CL3, nuclease S7 and cusativin, chemical cleavage methods using sulfuric acid (Jones et al., (1994) RNA Isolation and Analysis, chapter 3, Bios Scientific Publishers, Oxford) and physical methods using post source decay (Hahner et al., (1997) Nucleic Acids Res. 25:1957; Taniguchi and Hayashi (1998) Nucleic Acids Res. 26:1481; Kirpekar et al., (2000) RNA 6:296).

It will be understood that the 2'-OH modification may inhibit degradation of the polynucleotide. However, by empirically determining the sensitivity of the modified RNA to a range of conditions it will be/should be possible in most cases to select conditions that are suitable for chain cleavage. For example, it has been found that acetylated RNA is readily cleaved by nuclease Bal 31. Whilst alkali cleaves acetylated RNA it also results in acetyl cleavage so unless the amount of cleaved acetyl groups is measured by mass spectrometry, acetylated nucleotides will not be detected. For example, acid cleavage of the modified polynucleotide can be used for base sensitive modifications, whilst base cleavage can be used for acid sensitive modifications. It will also be understood that other degradation products such as dinucleotides, trinucleotides etc. will also be suitable for measuring the percentage modification of the polynucleotide. Whether it is the nucleotide, dinucleotide or larger fragments that are being measured, in each case it is the ratio of the number of fragments bearing a modification compared with the number of fragments not bearing a modification that provides the percentage modification.

Other methods that are capable of measuring high molecular weight RNA such as analytical ultracentrifugation to find the sedimentation coefficients (Svedberg units) are imprecise, require large amounts of starting material and are dependent on the conformation of the RNA (for review, see Jones et al., (1994) RNA Isolation and Analysis, chapter 3, Bios Scientific Publishers, Oxford). Despite these drawbacks, analytical ultracentrifugation using denaturing sucrose or isokinetic gradients may be useful to measure very large molecular weight changes in abundant RNA samples.

It is now much more common to measure the molecular weight of polynucleotides using electrophoretic separation in polyacrylamide or agarose gels. Detailed descriptions of the preparation, use and handling of electrophoresis gels is described in several publications (Sambrook et al., (1989) Molecular Cloning: A Laboratory Manual, CSH; Jones (1995) Gel Electrophoresis: Nucleic Acids Essential Techniques, Wiley). Denaturing gels are preferred to non-denaturing gels because they reduce conformational effects providing a means to measure the true molecular weight of the linear polynucleotide (Jones (1995) Gel Electrophoresis: Nucleic Acids Essential Techniques, page 47, Wiley). There are a variety of denaturants that can be used such as DMSO (50–90%), glyoxal (10–30%), formaldehyde (3% w/v), formamide (50–98%), heat (60–80° C.), methyl mercuric hydroxide (3–5 mM), sodium iodoacetate (10 mM), 2-pyrrolidone (5%) and urea (6–8 mM). It is known that incomplete denaturation of the polynucleotide leads to anomalous migration so that more than one denaturing condition may be required such as 8M urea plus 5% pyrrolidone or 8M urea run at 60° C. (Rosenblum et al., (1997) Nucleic Acids Res. 25:3925). Capillary electrophoresis provides an excellent means to carry out such molecular weight determinations and suitable methods have been described for RNA (Engel and Dieguez-Lucena (1993) Nucleic Acids Res. 21:759).

Comparative measurements of polynucleotide migration between different gels is difficult because the distance migrated is dependent on the buffer used, gel concentration and temperature. Therefore it is preferred that comparisons be made with both molecular weight standards and sample polynucleotides in the same gel. It is also known that certain percentages of the sieving matrix such as polyacrylamide or agarose are optimal for certain lengths of nucleic acids and above a certain percentage of acrylamide or length of polynucleotide (the exclusion limit) separation as a function of length does not occur. Therefore, measurements of the molecular weight should be made within such known limits (Sambrook et al., (1989) Molecular Cloning: A Laboratory Manual, CSH; Jones (1995) Gel Electrophoresis: Nucleic Acids Essential Techniques, Wiley).

It has been found that using a 20 cm 6M urea 5% polyacrylamide gel that a 250 nucleotide acetylated RNA runs approximately 20 mm apart from the non-modified form as a tight band. Therefore, measuring the amount of modification of smaller modifying groups than acetyl (42 daltons) should be feasible. The acetylated RNA also runs at a position predicted to be 100% modified as compared with RNA size markers.

It is common practice to be able to separate in a denaturing sequencing gel DNA polynucleotides differing by as little as 1 nucleotide in a total length of 500 nucleotides i.e. by 0.2% or less difference in length (Sambrook et al., (1989) Molecular Cloning: A Laboratory Manual, CSH.). It is therefore reasonable to expect that accurate measurements can be made for the molecular weight of RNA polynucleotides in their modified and unmodified forms when the modifying group is large, for example 28 daltons for formyl and 42 daltons for acetyl. Measuring the percentage modification with other modifying groups may also be possible providing that the molecular mass increase as a result of the modification is sufficient. For example, halogenation of the 2'-OH group should be readily measured for chlorine (35.4 daltons) and bromine (79.9 daltons) substitution of the 2'-OH group.

Calculating the percentage modification may be carried out by measuring the migration of known RNA size markers in a gel such as a 6M urea-5% acrylamide sequencing gel and plotting migration (mm) versus molecular weight (daltons) to obtain a standard curve. Because the exact, molecular weights of all the markers are known, it is straight forward to graph the relationship between the mobility in the gel versus the known molecular weight of each marker. The percentage modification for an RNA of known length with a known mass for the modifying group can then be readily calculated by comparison with this standard curve.

An alternative means to determine the percentage modification is to use a radioactively labeled reactant such as 14C or 3H acetic anhydride to modify RNA and then determining the molar ratio of radioactive acetyl groups to nucleotides in a known amount of RNA sample. If the molar ratio is 1:1, then 100% of the 2'-OH groups are modified. It will be understood that radioactive isotopes can be incorporated into a wide variety of reagents.

Regiospecificity of the reaction can be determined by subjecting an identical sequence of DNA (or preferably single stranded DNA bearing uracil as a replacement to thymine), to identical reaction conditions as used for RNA. It is expected that the DNA is not substantially modified as measured by incorporation of radioactivity, gel electrophoresis mobility, mass spectrometry, HPLC or any other analytical means used if the reaction is regiospecific for the 2'-OH group.

Modification at the 2'-OH position is preferably substantially regiospecific. Thus, there is preferably substantially no modification of the bases, phosphodiester bonds and/or any other position within the RNA chain. In this way, the polynucleotide retains important properties of the RNA. For example, advantageously, the polynucleotide is preferably modified so that a single strand of the polynucleotide is replicable by a nucleic acid polymerase to generate a second strand of polynucleotide complementary to the single strand.

The modification at the 2'-OH position may be such that the entire OH of the 2'C of the ribose ring is replaced by a reactant group R as in 2'-R or by OR having 2'-OR where the —O— group may or may not originate from the 2'-OH group. Accordingly, the substituent at the 2'-OH position in this case is R or OR respectively.

Various reactants or reactant combinations may be used, optionally in the presence of a catalyst, to provide these substituents, as described in further detail in the Examples below. Advantageously, the reactant comprises an acid anhydride, an acid halide, an acyl cyanide, a carboxylic acid or an N-acylimidazole, an alkoxyalkyl halide, an alkylthioalkyl halide, an alkoxyalkoxyalkyl halide, a trialkylsilane halide or a trialkylsilane imidazole. Each of these reactants participates in a modification (e.g. acylation, modification with an ether-containing group or with a silane) reaction with the RNA. Preferably, the reactant is attached to a solid phase such as with benzoyl chloride polymer bound beads (BCPB) so that the modification reaction at the 2'-OH group covalently links the RNA to the solid phase. Under these reaction conditions, the reaction medium may further comprise an acylation catalyst. For example, where the reactant comprises an acid anhyride, this may be reacted with the RNA in the presence of a catalyst such as a fluoride ion or amino pyridine. As a further example, where the reactant comprises an acid chloride or N-acylimidazole, the reactant may be reacted with the RNA in the presence of an amino pyridine. As a further example, where the reactant comprises a carboxylic acid, this may be reacted with the RNA in the presence of a dehydrating agent or a catalyst, such as an isocyanide catalyst. A preferred aminopyridine catalyst is dimethyl aminopyridine (DMAP).

The organic solvent used in the reaction medium of the present invention may comprise an organic base and may comprise an organic solvent in which is dissolved the organic base or, in another embodiment, may be the organic base itself. It is preferred that the reactant is soluble in the organic solvent. In a preferred embodiment the reaction medium further comprises water. In this way RNA to be modified may be conveniently added to the organic solvent as an aqueous solution of RNA. Typical organic solvents include alkanes such as hexane and pentane, pyridine, acetonitrile, dimethylformamide, dichloromethane, acetone, diethyl ether, benzene, chloroform, ethyl acetate, light petroleum, tetrahydrofuran, carbon tetrachloride, dichloroethane, dioxane, carbon disulphide, nitromethane, dimethyl sulphoxide, hexamethylphosphoric triamide and toluene. Typical organic bases include pyridine, triethylamine, trimethylamine, diisopropylethylamine, N,N-diethylaniline, N,N-dimethylaniline, 1,5-diazabicyclo (4,3,0)non-5-ene (DBN), 1,8-diazabicyclo(5,4,0)undec-7-ene (DBU) and N-methylmorpholine. Triethylamine $(CH_3CH_2)_3N$ is a stronger (non-aqueous base) amine base than pyridine, aniline, diethylamine or trimethylamine but less so than pyrrolidone. It is one of the strongest amine bases. A preferred organic base which acts as an solvent is triethylamine (TEA). Where a catalyst is to be used, it is convenient for the catalyst to be soluble in the organic solvent as well. The water and the organic solvent may form different phases in the reaction medium. For example, the water and the organic solvent may be immiscible with one another and form phases which will separate upon standing. Where there is more than one phase, the RNA may be reacted with the reactant under conditions of phase transfer catalysis.

The amounts of water and organic solvent may be varied and will depend to some extent upon the particular organic solvent/base/catalyst system to be used. Advantageously, the reaction medium comprises at least 50% organic solvent, preferably at least 80%, more preferably at least 90% and more preferably at least 95% v/v. Typically, the ratio of water:organic solvent is in the range 1:50 to 1:10, preferably around 1:20.

It should be noted that if the percentage of 2'-OH groups modified is low, then the remaining sites in the chain bearing non-modified 2'-OH groups will be sensitive to degradation. Degradation may be caused during the reaction if basic solvents such as triethylamine, ethyldiisopropylamine or pyridine are used. Low percentage modification may be caused for a variety of reasons. Bulky modification reagents such as pentanoic anhydride react more slowly than smaller reactants such as propanoic anhydride, possibly because of steric hindrance between the RNA polynucleotide and the reactant. It would be expected that even larger reactants such as octanoic anhydride or oleic anhydride or those reactants that react relatively slowly would also lead to partial 2'-OH modification. In some cases, partial 2'-OH modification is desired because the RNA retains many of its original biophysical properties. Partial 2'-OH modification can be favored over complete modification of the RNA by using large and bulky reactants, increasing the amount of RNA added, adding a competing reactive group, removing the catalyst, reducing the temperature and/or time of reaction or the amount of reactant present.

When the reactant itself is immobilized such as with benzoyl chloride polymer bound (BCPB) beads, it is unlikely that all the 2'-OH groups of a RNA polynucleotide will be modified because the RNA will be spatially constrained thereby restricting the other 2'-OH groups from contacting the other immobilized reactants. When partial 2'-OH modification is unavoidable or even desired, it is preferable to use reaction conditions that do not lead to RNA cleavage at non-modified sites such as by using non-basic solvents. It has been found that RNA in an intact form can be immobilized on BCPB beads when non-basic solvents such as tetrahydrofuran or dimethyl sulphoxide are used. If further protection/modification is desired, a second modifying reagent can be added during or subsequent to the first reaction thereby reacting and protecting the remaining 2'-OH groups. Alternatively, the secondary reactant could carry a label such as a fluorescent group (for example isatoic anhydride) allowing a simple means to quantitate the amount of RNA bound to the bead by measuring the amount of label subsequently attached to the RNA-beads. An example of such a secondary modification is given in the Examples.

In the absence of a catalyst, the reaction time is generally from 20 to 60 mins. In the presence of the catalyst, the reaction proceeds more quickly, the reaction time generally being completed within about 20 seconds.

On a vol/vol basis it is found that the ratio of reactant to reaction medium (especially acetic anhydride triethylamine/DMAP) is preferably in the range 1:200 to 1:10, more preferably around 1:20. Too little reactant gives a partial reaction and too much makes the reaction difficult to control.

In accordance with the method of the present invention, RNA is isolated from the sample by separating material which contains the substituent which has been used to modify the 2'-OH position of the ribose rings. Accordingly, a substituent needs to be selected so as to confer upon the RNA a property which the unmodified RNA does not possess. In one aspect, the substituent comprises an affinant capable of being recognized or bound by a partner such as a partner immobilized to a solid phase, or a protein. The affinant may be a hapten such as biotin or fluorescein which could be recognized and bound by an antibody or another protein such as streptavidin. Another useful affinant comprises a primary amino group capable of chemically reacting with an immobilized partner such as succinimide.

In one arrangement, the substituent comprises a hydrophobic substituent so that the RNA may be modified to render it more hydrophobic for the purpose of isolation. Both DNA and RNA are relatively hydrophilic molecules. It is quite difficult to separate RNA from DNA because their physical characteristics are similar. By increasing the hydrophobicity of RNA relative to DNA it is possible to improve the separation of the two types of nucleic acid. This is useful for either removing contaminating RNA from a DNA sample or removing contaminating DNA from RNA. For example it is important to remove bacterial RNA from a plasmid preparation prior to restriction enzyme analysis so that small DNA fragments are not obscured by the co-migrating RNA during agarose gel electrophoresis. Alternatively it is important to remove traces of DNA such as genomic DNA or viral DNA from cellular or viral RNA. Such DNA contamination often leads to false positives following RT-PCR amplification.

The hydrophobic substituent typically comprises a substituent, OR, wherein R comprises $C_1$–$C_{36}$ alkyl; $C_1$–$C_{36}$ alkenyl; $C_1$–$C_{36}$ alkynyl; $C_1$–$C_{36}$ haloalkyl; $C_1$–$C_{36}$ aminoalkyl; $C_1$–$C_{36}$ alkoxyalkyl; $C_1$–$C_{36}$ alkylthioalkyl; $C_1$–$C_{36}$ alkoxyalkoxyalkyl; $C_1$–$C_{36}$ haloalkoxyalkyl; $C_1$–$C_{36}$ aminoalkoxyalkyl; $C_6$–$C_{36}$ aryl; $C_6$–$C_{36}$ alkylaryl; $C_6$–$C_{36}$ arylalkyl; $C_6$–$C_{36}$ arylalkenyl; $C_1$–$C_{36}$ alkanoyl; $C_1$–$C_{36}$ alkenoyl; $C_1$–$C_{36}$ haloalkenoyl; $C_1$–$C_{36}$ haloalkanoyl; $C_2$–$C_{36}$ haloformylalkanoyl; $C_1$–$C_{36}$ aminoalkanoyl; $C_1$–$C_{36}$ azidoalkanoyl; $C_1$–$C_{36}$ carboxyalkanoyl; $C_1$–$C_{36}$ carboxyalkenoyl; $C_1$–$C_{36}$ carboxyalkynoyl; $C_1$–$C_{36}$ alkylaminoarylalkanoyl; $C_1$–$C_{36}$ alkoxycarbonyl; $C_1$–$C_{36}$ alkenyloxycarbonyl; $C_1$–$C_{36}$ alkylsulfonyl; $C_6$–$C_{36}$ arylalkanoyl; $C_6$–$C_{36}$ arylalkenoyl; $C_6$–$C_{36}$ aryloxyalkanoyl; $C_6$–$C_{36}$ alkylarylalkanoyl; $C_6$–$C_{36}$ haloarylalkanoyl; $C_6$–$C_{36}$ aminoarylalkanoyl; $C_1$–$C_{36}$ alkylsilanyl; $C_1$–$C_{36}$ trialkylsilanyl or $C_{12}$–$C_{28}$ diarylphosphano; or a substituent R', wherein R' comprises $C_1$–$C_{36}$ alkyl; $C_1$–$C_{36}$ alkenyl; $C_1$–$C_{36}$ alkynyl; $C_1$–$C_{36}$ haloalkyl; $C_1$–$C_{36}$ aminoalkyl; halo; amino; $C_1$–$C_{36}$ alkylamino; $C_6$–$C_{36}$ aryl; $C_1$–$C_{36}$ alkylaryl or $C_1$–$C_{36}$ arylalkyl.

In one embodiment, the hydrophobic substituent comprises a $C_4$–$C_7$ carbon chain or ring, preferably one which arises where the reactant comprises butyric anhydride, pentanoic anhydride, hexanoic anhydride or benzoic anhydride. In this case, it is preferred that the proportion of 2'-OH groups bearing the substituent is at least 10%.

Alternatively, the hydrophobic substituent may comprise a $C_8$–$C_{12}$ carbon chain or ring in which case it is preferred that the proportion of 2'-OH positions bearing the substituent is in the range 1 to 10%. As a further alternative, the hydrophobic substituent may comprise a $C_{12}$–$C_{36}$ carbon chain or ring more preferably a $C_{12}$ to $C_{24}$ carbon chain or ring. In this case, it is preferred that the proportion of 2'-OH positions bearing the substituent is up to 1%. Thus, whilst modification of up to 1% may provide a sufficiently hydrophobic modified RNA where a long chain length of substituent is used, substituents of lower carbon chain length require a higher percentage, perhaps in the range up to 95%, to be effective.

A number of methods for isolating RNA from samples treated in accordance with the present invention exist. For example, the step (b) of separating material containing the substituent from the sample may comprise contacting the treated sample from step (a) with a hydrophobic solid phase so as to bind the material containing the hydrophobic substituent and optionally washing the material bound to the hydrophobic solid phase. The hydrophobic solid phase may comprise hydrophobic particles. This method may further comprise a step of eluting the material bound to the hydrophobic solid phase by treating with a detergent, a chaotrope or a solvent, by lowering the salt concentration or by cleaving the substituent from the 2'-OH position of the ribose rings.

In a further embodiment, step (b) comprises treating the treated sample from step (a) with a lyotrophic salt to aggregate the material containing the hydrophobic substituent as an RNA precipitate, and isolating the precipitate. The lyotrophic salt preferably comprises ammonium sulphate, an alkali metal chloride, magnesium chloride or calcium chloride.

In a further embodiment, step (b) may comprise treating the treated sample with a non-polar solvent to form the hydrophobic liquid phase which contains the material containing the hydrophobic substituent, and isolating the hydrophobic liquid phase. The non-polar solvent typically comprises pentane, cyclohexane, toluene, benzene, light petroleum, xylene or hexane.

In a further embodiment, step (b) may comprise use of a membrane, such as a PVDF membrane, to separate the RNA. The addition of hydrocarbon chains to the 2'-OH position of RNA increases its hydrophobicity, that is its ability to interact with a hydrophobic surface. The use of hydrophilic PVDF filters to purify RNA has already been described in U.S. Pat. No. 5,958,677 (September 1999). However, this describes only the binding of RNA, which is in its unaltered form is a weakly hydrophobic molecule. Modified RNA molecules of increasing hydrophobicity can be created, as discussed above, by adding acyl groups of increasing chain length. Hydrophobicity increases in the order: 2'-OH<formyl(—C(O)H)<acetyl(—(O)CH$_3$)<propanoyl(—(—C(O)CH$_2$CH$_3$)<butanoyl(—C(O)CH$_2$CH$_2$CH$_3$), i.e. according to the carbon chain length. Longer chain lengths than butanoyl were not tested but would be expected to follow the same trend. The increase in the strength of the hydrophobic interaction was tested by binding RNA and modified RNA to a polyvinylidene fluoride (PVDF) membrane and subjecting the bound material to increasingly stringent wash conditions (see Examples).

The reagent modifying the RNA 2'-OH group may be either free in solution or attached to a solid phase. In a particularly preferred aspect of this invention, a solid phase is employed. In this embodiment, the solid phase is not the same as the hydrophobic solid phase described above and is used as a reactant so that the solid phase itself is introduced as the substituent modifying the RNA (note the hydrophobic solid phase is employed only after the RNA is modified with a hydrophobic substituent). When using a solid phase, the modification reaction will lead to the covalent attachment of the RNA to the solid phase. This provides a convenient means to immobilize RNA to a solid phase in order to purify or analyze it. For example, RNA will be preferentially bound to the solid phase from a RNA, DNA and protein mixture such as a cell lysate or serum.

Advantages of using RNA covalently bound to a solid phase include ease of manipulation, purification, automation and compatibility with many important life science applications such as diagnostics and detecting gene expression. It is also a convenient means to limit the amount of modification occurring on the RNA polynucleotide because the reactive groups are spatially restricted. RNA modified at only a few 2'-OH positions may retain important biological functions such as serving as a template for protein translation, hybridization and serving as a template for a polymerase.

There are many potentially useful solid phase reactants (see review by Akelah and Sherrington (1981) Chem. Rev. 81:557) such as other carboxylic acid derivatives including acid halides and acid anhydrides. Benzoyl chloride polymer bound (BCPB) beads are commercially available (Fluka, USA) with high densities of benzoyl chloride groups (approximately 2.1 mmol/g of resin). RNA can be covalently attached to the benzoyl chloride solid support via an ester linkage between the BCPB bead and the 2'-OH group. Under appropriate reaction conditions, the 2'-OH groups of the RNA will react with the benzoyl chloride and become covalently coupled to the solid phase. Due to the physical separation of the benzoyl chloride groups, it is highly unlikely that all (100%) of the 2'-OH groups of a polynucleotide will be modified, rather only one or a few will be modified per polynucleotide. In order to immobilize RNA, it is sufficient that only one 2'-OH group reacts with the solid phase reagent.

Other solid phase reactive groups that may be suitable for immobilizing RNA could include acid anhydrides. In the case of acid anhydrides it is important that the half of the acid anhydride attached to the solid phase is the part that reacts with the 2'-OH group thereby immobilizing it. Otherwise, the result will be modified RNA in solution. In order to overcome this potential problem, an asymmetric acid anhydride may be attached to the solid phase so that the half of the acid anhydride attached to the solid phase reacts preferentially with the 2'-OH group resulting in immobilized RNA. Other examples include the use of cyclic anhydrides such as isatoic anhydride polymer bound (Cat 17344, Fluka, USA). However, it is simpler to employ carboxylic acid derivatives such as the acid halides (e.g. benzoyl chloride polymer bound), acid cyanides (e.g. benzoyl cyanide polymer bound) or acid imidazoles (e.g. N-benzoyl imidazole polymer bound) because the outcome of the reaction will be an ester linkage between the solid phase and the polynucleotide.

It will be understood that the solid phase reactant need not be limited to carboxylic acid derivatives, rather any reactant that reacts with the 2'-OH group in a regiospecific manner is suitable. The amount of particles required to immobilize a given amount of RNA will depend on several factors such as the density of the reactive groups and the proportion of the reactive groups that will react with the 2'-OH. Reactive groups that are buried, for example within the resin will be unable to react with a large molecule like RNA and they will therefore be effectively unreactive. The precise RNA binding capacity for a particular solid phase reactant will require empirical tests. If steric hindrance occurs between the polynucleotide and the reactive group due to the proximity of the solid phase a linker or spacer may be used between the solid phase and the reactive group such as —(CH$_2$)$_{12-16}$.

The solid phase may consist of an inorganic particle, a polymeric linear, globular or cross-linked molecule or resin. It may be made of a variety of materials or material composites such as acrylamide, agarose, cellulose, polyamide, polycarbonate, polystyrene, latex, glass and silicon. It may also possess specific properties that aid in the manipulation of the particle such as paramagnetic or magnetic properties, a diameter allowing retention by a filter, an increased density that enhances sedimentation or separation by centrifugation or incorporate a tag aiding identification, capture or quantification of the particle.

The tag may be colored, fluorescent, an isotope, an epitope for an antibody or a ligand for a protein such as streptavidin, or a protein such as an enzyme or antibody or an oligonucleotide. One purpose of the tag is to aid identification of the particle when particles from several sources are combined. For example, if mRNA from tissue 1 is immobilized on particle type A, mRNA from tissue 2 is immobilized on particle type B and particles A and B are then mixed and added to a hybridization reaction including for example a radioactive probe. Following hybridization, particles of type A and B are separated by means of a property unique to the tag and the radioactivity associated with each particle analyzed to provide a measure of the relative gene expression in tissues 1 and 2. Other uses of the tag could include the automated quantification and validation of the number of particles in a vessel such as a 96-well plate.

The 'particle' or macromolecular structure may be incorporated into many forms such as a strip, a fiber, a matrix, a membrane, a filter, a column, a bead, a resin, a vessel wall, a pipette tip, a gel or a plate or an etched silicon device.

The reactant may be covalently attached to the solid phase using for example divinyl benzene (DVB) or associated by another means such as ionic interaction or hydrogen bonding so that in any case the RNA is firmly held to the solid phase during washing and analysis. However covalent attachment is preferred because there will be less tendency for the reactant to dissociate from the solid phase. The solid phase reactant may be incorporated into a microdevice or vessel such as those made from etched silicon and the solution containing the RNA passed over or through the region containing the reactant so that RNA immobilization occurs in a specific region of the solid phase. This process may be automated in order to detect for example RNA viruses such as HCV and HIV in blood or body fluids. The immobilized sample might then be used for any number of down stream applications such as hybridization, RT-PCR, TMA or NASBA.

Alternatively, the solid phase reactant may be incorporated into a blood collection device such that the RNA components of the blood are immobilized during the blood collection process. The solid phase reactant may also be coated or attached to a glass slide in many small (preferably less than 1 mm$^2$) discrete regions. A single RNA sample from, for example a tissue source may be added (in a suitable solvent and catalyst) to one of the discrete regions thereby localizing the RNA to a discrete position of the glass slide. The process may then be repeated with other RNA samples until tens, hundreds or thousands of RNA samples are attached to as many discrete regions of the slide as necessary. The slide could then be washed and subjected to hybridization conditions with a labeled probe representing the sequence of interest such that multiple hybridization events could be detected and with suitable instrumentation, quantitated on a single slide. Such microchip applications could have very broad applications such as diagnostic or gene expression analyses.

For certain applications it may be useful to restrict the size of the RNA that is immobilized. By using a macroporous resin with the reactant located within the pores, a size cut-off is established whereby only smaller RNA polynucleotides will be capable of accessing and therefore reacting with the reactant whilst longer RNA polynucleotides are lost. This could be useful for determining the size of the RNA polynucleotides being analyzed. Alternatively it may provide a means to specifically remove short RNA polynucleotides allowing the separation of longer complete RNA polynucleotides that do not react with the solid phase. Separation of RNA based on size is currently carried out using either gel electrophoresis or column chromatography and this invention provides a simpler means to remove short polynucleotides from solution. Commercial sources of beads with defined pore sizes are available for oligonucleotide synthesis.

Following immobilization to the particle, the RNA may be further modified at the remaining 2'-OH positions in order to endow it with additional desired properties such as hydrophobicity, fluorescence, radioactivity or nuclease protection. The RNA may also be used for a variety of quantitative assays such as hybridization with labeled probes or serve as a template for RT-PCR. In the latter case, it has been found that BCPB beads have the advantage of being compatible with both the components of the reverse transcription and PCR reactions. Other purification materials such as silica beads inhibit these reactions.

A marked advantage of using BCPB beads compared with silica beads to purify RNA is that there is no elution step required to separate the RNA from the solid phase. If silica beads are added to the reverse transcription reaction they would bind both the template RNA, primers and a proportion of the enzyme leading to reduced or total inhibition of cDNA synthesis. It has been found that following RNA reaction, BCPB beads can be added directly into both the reverse transcription and PCR reactions with no such inhibition. BCPB beads may also find utility for other types of reactions such as LCR and NASBA. Adding the beads to the reaction simplifies manipulation and ensures that all the captured RNA is transferred into the reaction. The bead format could prove useful for automated systems in the diagnostic field. Thus BCPB beads are especially preferred in the present invention.

Solvents:

When RNA is modified using acetic anhydride in a basic solvent such as triethylamine with DMAP, the modification of the 2'-OH groups proceeds so quickly that base catalyzed cleavage of the RNA is insignificant. However, when the reactant is attached to a solid phase such as the BCPB, it is unlikely that all the 2'-OH groups can be modified due to the physical immobilization of the reactant. Therefore, even after extensive incubation times, the majority of the 2'-OH groups will not be modified and are therefore susceptible to cleavage by the basic solvent. It is very important that the solvent used does not lead to RNA polynucleotide cleavage. Preferred non-basic solvents include tetrahydrofuran and dimethyl sulphoxide. Neither of these solvents results in RNA cleavage yet both the RNA and catalysts such as DMAP readily dissolve in it.

It was found that some solvents increased the amount of BCPB bead sedimentation under unit gravity thereby decreasing the contact between the bead and solvent bearing the RNA. Both THF and DMF allowed the beads to be well dispersed in solution whilst water, DMSO, pyridine, triethylamine and ethyldiisopropylamine (EDPA) promoted sedimentation. This may be an effect of both density differences between the bead and solvent and hydrophobic interactions between the beads themselves. Preferred beads increase the contact between reactant and the solvent containing the RNA.

Amount and Size of Beads:

It was found that adding a large excess of beads reduced the amount of RNA bound to the BCPB. For 50 ng of RNA in 1 μl of water, added to 80 μl of THF/DMAP (5 mg/ml) adding more than 1.5 mg of BCPB reduced the percentage of RNA bound from 74% to 48% (22 mg BCPB). It was found that during post-reaction purification of the BCPB beads that they tended to clump and stick together in aqueous solution making washing the beads difficult. This problem was overcome simply by stopping the reaction with 3 reaction volumes of 70% ethanol and briefly mixing before washing with aqueous solutions. Preferred bead sizes are those that provide a maximum surface area for reaction to occur with the RNA. Buried reactive groups will not be accessible to the RNA, therefore beads and particles with a small diameter (large surface area to volume) are preferred. However, in order to collect the beads from the liquid phase it is necessary that they are not so small that they cannot be easily pelleted by centrifugation, collected by filtration or selected by other means. Commercially available BCPB beads with a mesh size of 100–300 are readily pelleted using a centrifugal force of 1500 g for 5 sec.

Length of RNA Suitable for RT-PCR:

Due to the physical separation of the reactive groups on the solid phase, a single RNA template may be linked to the solid phase via only one or a few 2'-sites. If the RNA template is relatively long and the sequence to be amplified relatively short, there will only be a small number of RNA templates that are attached within the sequence to be amplified. These templates will probably not be copied by the enzyme because the2'-modification may block the passage of the enzyme. The HCV RNA genome is approximately 10,000 nucleotides long, if the PCR primers span a region of 100 bp, only 1% of the polynucleotides will not amplify due to the2'-modification. However, if the RNA template is shorter, for example 1000 nucleotides and the PCR primers span 1000 bp, then none of the RNA will serve as a template for RT-PCR. It is therefore preferable to PCR amplify only short regions of the RNA. Furthermore, the reverse transcriptase primer should be as close to the 3' PCR primer as possible, preferably being of identical sequence. However, for RT-PCR analysis of mRNA where the cDNA synthesis has to be primed using an oligo (dT) primer, it is preferable to use PCR primers that amplify sequences close to the 3' end of the mRNA. Alternatively the RNA may be released from the solid phase using chemical or enzymatic deprotection, for example by alkali or KCN cleavage of the ester linkage before RT-PCR.

DNA Binding:

Under specific conditions, some DNA will bind non-specifically to the beads probably through hydrophobic interactions with the BCPB bead. Such interactions can be reduced by using DMF, pyridine, ethyldiisopropylamine (EDPA), triethylamine or DMSO as the reaction solvent instead of THF. Non-specific DNA binding can be removed by one or more washes in 10% SDS. However, DNA may react with BCPB beads covalently via either the3' or 5'-OH groups. Less than 3% of a labeled DNA sample became covalently attached when DMSO was used as a solvent for the BCPB beads compared with 14% with THF as a solvent.

Protein Binding and Diagnostic Systems:

In a similar manner to DNA, some protein will bind to BCPB. It was found that adding detergents to a THF solvent containing $^{35}$S-labelled cellular protein enhanced the amount of protein binding to the beads. This may be caused by the detergent unfolding the protein and therefore exposing more hydrophobic residues to the BCPB. The greatest enhancement was seen with a final concentration of 0.025% TWEEN/NP-40 detergents, THF and protein were mixed and incubated 3 min at 22° C. with 3 mg of BCPB. Protein binding could be reduced by 50% by pre-reacting the protein with acetyl chloride. Protein binding to BCPB was not reduced if the reactivity of the benzoyl chloride group was neutralized with water prior to addition of protein. This suggests that protein binding is occurring non-specifically probably by a hydrophobic interaction.

When RNA was purified from solutions containing high concentrations of protein, it was found that a proportion of the RNA tended to bind to the beads whilst complexed with protein in a non-specific manner. Such RNA could be readily removed by several washes in 10% SDS.

It was found that highest RNA binding to BCPB beads took place when the protein and RNA were added separately to the THF solvent rather than prior to mixing with the solvent. The beads were then added last and the reaction mixed and incubated.

A practical solution to non-specific protein binding to the BCPB beads may be the use of a protein removal step before the addition of the BCPB beads to the sample. For example this may consist of a protein pre-binding step: a serum sample containing the RNA analyte may be added to, or passed through a protein binding surface such as a hydrophobic bead, membrane, filter or other protein capture surface and then the solution containing the deproteinised RNA added to the reactant-solid phase such as BCPB beads. Suitable membranes that are known to capture proteins but not nucleic acids include 0.45 µm pore size IMMOBILON-P (hydrophobic polyvinylidene fluoride, Millipore, US). Alternatively, proteins could be separated from an RNA virus by filtration whereby the proteins but not the virus particles pass through an ultrafiltration membrane with a nominal molecular weight cut-off of 30,000–100,000 daltons such as CENTRICON-100, CENTRIPLUS-100 (Amicon, US). Filters with pore sizes above 0.01 µm such as ISOPORE 0.05 µm polycarbonate membranes (Millipore, US) should generally capture most virus particles from blood serum whilst allowing most proteins to pass through. Such collected virus particles could then be added to the reactant-solid phase such as BCPB beads.

The volume of a body fluid such as serum may be reduced prior to addition of the reactant-solid phase using a CENTRIFREE filtration device. The retained sample containing protein and viral RNA could then be added to a solvent containing the reactant-solid phase such as BCPB beads.

Blood contains approximately 70 mg/ml of protein and a large component of this is albumin and immunoglobulins. Means to reduce serum proteins include the addition of immobilized *S. aureus* protein A or thiophilic resin (Sigma, US) which bind immunoglobulins, a major component of blood protein. Protein A linked to a solid phase such as a bead or thiophilic resin would provide a facile means to reduce blood protein concentration.

Enhancing the Reaction:

The RNA binding reaction may be enhanced by reducing the volume of the reaction to a minimum required to keep the RNA soluble and in contact with the beads. Approximately 10 µl of solvent is required to immerse 1–3 mg of BCPB. It was found that adding plasmid DNA to a final concentration of 25 ng per microlitre enhanced RNA binding, possibly by increasing the apparent concentration of the RNA. Other volume excluding compounds such as polyethylene glycol may also enhance RNA binding.

Addition of Detergents and Chaotropes:

In order to increase specific RNA binding whilst reducing protein binding, detergents were added to a reaction containing BCPB beads in different solvents. It was found that the addition of a final concentration of 1% SDS in DMSO or THF increased the amount of RNA bound to BCPB by 33% and 42% respectively whilst 1% SDS in DMF or toluene markedly reduced RNA binding. It was also found that except for toluene, a final concentration of 1% SDS increased the amount of $^{35}$S labeled cellular protein bound to BCPB in DMF, DMSO and THF by 6.8, 2.3 and 1.85 times respectively that of a parallel reaction containing no added SDS. EDPA, pyridine or water led to low levels of RNA binding.

It was found that addition of 150 mM sodium perchlorate (final concentration) to 40 µl DMSO containing 3 mg BCPB beads, 10 µg BSA and 20 ng of radiolabelled RNA increased the amount of RNA bound by 2.3 fold. Even lower sodium perchlorate concentrations of 1.5 mM and 15 mM (final concentration) increased RNA binding by 1.11 and 1.33 fold respectively. This effect was not caused by the high salt concentration because a parallel reaction containing 125 mM NaCl instead of sodium perchlorate bound 30% less RNA.

The addition of sodium perchlorate also increases the amount of protein bound to the beads. 40 µl of DMSO containing 3 mg BCPB beads was mixed with 1 µl of $^{35}$S labeled cellular protein with either 1 µl of water or with 1.5 mM, 15 mM or 150 mM sodium perchlorate (final concentration), protein binding increased by 0, 1.38 and 1.5 times respectively with sodium perchlorate.

However, 600 mM urea or 400 mM guanidine thiocyanate in THF reduced BCPB reactivity by 39% and 73% respectively. The addition of chaotropes and/or detergents is important because if RNA is to be isolated intact from cells, blood or other biological material, it is necessary to inhibit ribonuclease activity. One way to do this is to use a slight excess of chaotrope and/or detergent and then add this to the solid phase reactant in a suitable solvent system thereby immobilizing the RNA. The solid phase may then be washed to remove contaminating proteins and DNA. Suitable chaotropes may include guanidinium chloride, guanidinium thiocyanate, sodium iodide, sodium perchlorate and sodium trichloroacetate.

An aliquot of BCPB stored at 22° C. was opened over the course of 3 weeks and exposed to the air approximately 30 times. No reduction in reactivity was noted. BCPB is thus sufficiently stable for the present applications. Water in excess of 7.5% vol/vol in THF reduces the reactivity of BCPB. The preferred water content is 3 µl or less in 40 µl of THF with 1 mg of BCPB.

To reiterate, in addition to the preferred BCPB beads, the solid phase could include a particle, a bead, a membrane, a gel, a slide or cover slip, an etched silicon surface, a fiber, a filter, a capillary, a tube, a vessel or a multi-vessel plate such as a 96 well plate. It will be apparent that the use of a solid phase improves handling throughput and accuracy when the RNA immobilization and analysis is automated. In this context, paramagnetic particles are favored for their handling properties. Other preferred solid phases are those which comprise OH groups, e.g. compounds of silicon and oxygen, such as silica particles or a glass. Nucleic acid purification using silica beads is well known and widely practiced both in diagnostic and life science research. Methods of purifying RNA have been described in U.S. Pat. No. 5,234,809. Briefly the method involves binding the nucleic acid sample to silica beads in a chaotropic agent such as urea and then washing the beads in a high salt wash before it is eluted into water. The modified RNA used in the present invention has been tested for its ability to bind and be released from silica beads using a silica bead purification kit (Qiagen, Germany) and found to be particularly suited to this type of separation method (see Examples).

As mentioned above, according to U.S. Pat. No. 5,234,809, the purification of nucleic acids from biological samples involves mixing silica particles with a chaotropic salt containing the sample. Under these conditions the nucleic acid binds reversibly to the silica. During attempts to find new methods to separate modified RNA from the reaction components, it has been discovered that modified RNA will readily bind to silica beads, e.g. in the presence of 95% organic solvent. This unexpected result suggests that silica particles are suitable to bind modified RNA from a variety of organic solvents.

Agents may be employed to aid in binding the RNA to the solid phase. Bifunctional acid halides, e.g. acid chlorides, are commercially available that have effectively two reactive groups per molecule. Reagents such as sebacoyl chloride $(ClOC(CH_2)_8COCl)$, adipoyl chloride $(ClOC(CH_2)_4COCl)$ and glutaryl chloride $(ClOC(CH_2)_3COCl)$ can be used to immobilize RNA by covalent modification of the 2'-OH group with consequent attachment to a solid phase. The bifunctional acid chloride can either be reacted with the RNA and then with a solid phase, or preferably with a solid phase and then the RNA sample. In both cases, the solid phase is conveniently BCPB beads, or one which has hydroxyl groups such as glass and other silicon dioxide compounds. It is known that boiling concentrated HCl exposes hydroxyl groups on the surface of glass. Such prepared glass can then be reacted with an excess of the bifunctional acid chloride, the unreacted acid chloride is removed by washing in solvent such as THF and then the RNA sample added and allowed to react with the immobilized acid chloride, thereby becoming immobilized via the acid chloride to the glass solid phase. Bifunctional acid chlorides are preferred that have an extended hydrocarbon spacer between each end of the molecule such as with sebacoyl chloride (Cat. No. 84848 Fluka, USA) because these are likely to reduce steric hindrance between the RNA and the solid phase and therefore improve the reaction.

Modification of RNA whilst bound to silica beads: Nucleic acids become bound to the surface of silica beads, therefore tests were carried out to find out whether RNA can be modified whilst bound to the silica beads. Although it may be expected that some of the 2'-OH groups are protected from modification due to steric hindrance between the silica bead and the RNA, in practice, this effect was found to be undetectable leading to substantially modified RNA (see Examples). When modifying with acetic anhydride, for example, compared with an RNA modification reaction with no acetic anhydride added, the modified RNA was substantially intact and migrated identically to an acetylated RNA modified by the standard procedure. Modification, such as acetylation, of RNA can therefore occur whilst the RNA is bound or attached to a solid support or surface. This potentially offers advantages when high throughput of samples is required or when RNA is purified using silica beads for example for diagnostic purposes from blood. This is therefore a preferred aspect of the present invention.

In a further aspect, the present invention provides a kit for isolating from a sample RNA comprising an oligo- or polynucleotide, which kit comprises:

(i) a reaction system for modifying the RNA to form a modified oligo- or poly-nucleotide in which a proportion of the 2'-OH positions of the ribose rings bear a substituent; and (ii) a separation system for separating material containing the substituent from the sample, so as to isolate the RNA.

Preferably, the Reaction Systemcomprises:

(a) an organic solvent; and (b) a reactant capable of covalently modifying the 2'-OH position of the ribose rings of the RNA in the presence of the organic solvent. The organic solvent and reactant are discussed in further detail above.

The present invention will now be described in further detail, by way of example only, with reference to the following examples.

General Procedure:

A complex mixture of DNA and RNA polynucleotides from a cellular source is treated with a lipophillic acid anhydride such as butyric anhydride $(C_8H_{14}O_3)$, pentanoic anhydride ($C_{10}H_{18}O_3$), hexanoic anhydride ($C_{12}H_{22}O_3$), heptanoic anhydride ($C_{14}H_{26}O_3$) or benzoic anhydride ($C_{14}H_{10}O_3$) as described. Longer chain lengths than heptanoic anhydride are not preferred for complete (100%) RNA modification because incomplete modification of the RNA chain has been observed, possibly due to steric hindrance between the RNA chain and the long chain anhydrides. Such reagents will modify the single terminal 3'-OH group and possibly the single 5'-OH or phosphate group of the DNA or RNA chain but all or substantially all the 2'-OH groups of the RNA, thereby strongly altering the physical characteristics of the RNA towards lipophilicity. However the DNA is modified at only one (3'-OH) or a maximum of two (one 5'-OH/phosphate and one 3'-OH) position(s) and therefore remains overall hydrophilic. This difference in lipophilicity then serves as the basis for separation of the DNA from RNA.

The hydrophobic RNA is preferably manipulated with silanised plasticware and/or with detergents such as 0.01% TWEEN-20, 0.01% NP40 or 0.1 TRITON X-100 so that sample loss is reduced.

The capture surface or material for the modified RNA could be encapsulated within a centrifuge device such as a microcentrifuge spin-column or tube insert. Alternatively, it could be encapsulated in a pipette tip such as those commonly used to measure 1 µl, 10 µl, 200 µl or 1 ml volumes. In either case, capture, washing and elution of the modified RNA is improved because the time required to separate the modified RNA from the contaminants is reduced.

Multiple RNA samples could be purified in parallel by the use of devices bearing multiple capture surfaces. An example would be a 96-well plate whereby each well is hydrophobic and suitable for capture, washing and elution of one modified RNA sample. A further example would be a vessel or chamber suitable for the modification reaction and in addition the capture, washing and elution of the RNA sample. In this way, both the modification and purification is carried out in the same vessel or chamber improving sample throughput and productivity. The modification, capture, washing and elution of the RNA sample could be automated and involve robots.

Methods of treatment of the RNA are described in further detail in UK patent applications, nos. 9910154.5 entitled POLYNUCLEOTIDES published 30 Jun. 1999 as GB9910154A, 9910157.8 entitled POLYNUCLEOTIDES published 30 Jun. 1999 as GB9910157A and 9910156.0 also entitled POLYNUCLEOTIDES published 30 Jun. 1999 as GB9910156A. Each of these copending patent applications was filed 30 Apr. 1999 in the name of the same applicant. For example, Example 6 of each of these copending patent applications sets out one preferred method of modifying RNA involving a DMAP-catalysed acetylation reaction. The methodology in that Example may be modified using instead of acetic anhydride, anhydrides of longer chain length including butyric or pentanoic anhydrides as set out in Example 54 of each of the copending applications. In addition, Example 1 of each of these copending patent applications sets out a method of modifying a total cellular RNA population and selection of the mRNA fraction.

It will also be apparent to those skilled in the art that a crude cellular or tissue lysate consisting of RNA, DNA, protein and lipids etc. may serve as the sample for the modification reaction. In this case, the reactant may modify not only the 2'-OH group of the RNA chain but also the hydroxyl bearing side chains of the amino acids tyrosine, serine or threonine of proteins. It will be apparent that such a reaction is beneficial because it will lead to the deactivation of cellular nucleases and therefore allow the selection of RNA in a more intact form. Furthermore, cells could be disrupted in the presence of the reactant so that nucleases are immediately inactivated on release from the cell and the RNA is immediately modified and therefore protected from any remaining nucleases. In this latter case, increased concentrations of the reactant in the reaction may be required in order to inactivate the nucleases fully as well as to modify fully the 2'-OH groups of the RNA sample.

The treated DNA and RNA sample in a high salt buffer (e.g. 1–5 M ammonium sulphate, preferably 10 mM phosphate, pH 7.0, 1.5 M ammonium sulphate) is passed over a hydrophobic column as is commonly used for reverse phased liquid chromatography. For example reversed phase packings based on silica may have bonded hydrocarbon chains of C4, C8 or C18 or others may be based on polystyrene (e.g. POROS® and OLIGO R3, PerSeptive Biosytems, USA) may be used under appropriate conditions. Further alternatives could include plastics such as polypropylene, polycarbonate, polyvinylidene fluoride (manufactured under the tradename HYDROPHOBIC DURAPORE, (Millipore, USA) and PTFE. With all plastics those with a large surface area to volume are preferred in order to increase the effective hydrophobic binding surface. These types of surfaces exist as beads of cellulose covered with butyl, octyl or phenyl groups (CELLUFINE BUTYL, CELLUFINE PHENYL and CELLUFINE OCTYL, Amicon, Mass, USA) and are well known in the art. Other bead compositions could include silica matrix modified with polyethylene-imine (SI PAE, Amicon, Mass, USA). After washing extensively with water to remove all traces of DNA, the RNA can be released by several methods. Firstly and preferably, the RNA can be deprotected by cleavage of the modifying group with 50% ammonia treatment, 10–40 mM KCN (final concentration) in 95% EtOH, $K_2CO_3$ in aqueous methanol or other conditions which are known to lead to the cleavage of the ester linkage (see Protective Groups In Organic Chemistry, $2^{nd}$ edition, Ed. T. W. Greene, Wiley-Interscience). The RNA can then be collected and purified further if required by, for example oligo (dT) selection of the mRNA.

Alternatively the RNA can be removed from the solid support in its modified form using detergents such as 0.1% SDS, 0.002M TRITON X-100™ (Union Carbide Chemical and Plastics, Inc.), NONIDET P-$_{40}$™ (Shell Oil Co.) or 1% TWEEN™ (ICI Americas, Inc.) in aqueous solution. Or alternatively by lowering the salt concentration (preferably 10 mM phosphate, pH 7.0) in the binding buffer to a point where elution is brought about. Another approach is the addition of a chaotropic agent such as ethylene glycol, urea, guanidine-HCl or thiocyanate salts. Solvents such as isopropanol, methanol, ethanol, DMSO or acetonitrile may also be used to elute the RNA up to a final concentration of 40% (v/v) in water.

The invention will now be described in further detail, by way of example only, with reference to the following Examples and the accompanying drawings, in which:

DETAILED DESCRIPTION OF THE INVENTION

EXAMPLE 1

Use of Lyotrophic Salts

Separation can be brought about using such commonly used salts as ammonium sulphate or sodium chloride (known as <<lyotrophic salts>>) which are routinely used for separating proteins with varying hydrophobic properties from solution by a process known as 'salting out'. Proteins with the greatest hydrophobic tendencies aggregate and precipitate out of solution at the lowest lyotrophic salt concentration. By comparison with this system it will be apparent that a specific salt concentration can be selected that will cause modified RNA to aggregate whilst the hydrophilic DNA will remain in solution thereby providing the basis for separation. The specific salt concentration will depend on the particular modifying reagent used. For example, RNA modified with longer carbon chains which are therefore more hydrophobic such as heptanoic anhydride will aggregate at a lower salt concentration than those modified by shorter chain lengths such as acetic or propionic anhydride. Other salts that may be used (in order of decreasing ability to cause RNA to aggregate) include RbCl, KCl, NaCl, CsCl, LiCl, $MgCl_2$ and $CaCl_2$.

Aggregates can be collected either by allowing precipitation to occur at unit gravity or by centrifugation at 1–5000 g in a bench top centrifuge. The modified RNA can then be collected and salts removed by washing with several washes of 70% ethanol. Alternatively, salts can be removed by using a CENTRICON-50 column (Amicon, MA, USA) and washing with a either water or 0.1% SDS. Following this purification procedure and, alternatively following the removal of the hydrophobic group, the RNA may be used as a template for RT-PCR or in northern blotting.

EXAMPLE 2

Partition Between Two Solvents

As another alternative separation procedure, modified RNA with increased hydrophobic properties could be simply purified from a complex mixture of proteins, DNA and other cellular components by mixing and agitating by use of a vortex etc. the mixture with appropriate solvents such as (in order of decreasing polar property) pentane, toluene, chloroform, THF, DMSO or methanol. Under ideal conditions it would be expected that all the modified RNA would partition into the hydrophobic phase whilst non-RNA contaminants would remain in the aqueous phase. Simple separation of the hydrophobic phase by pipetting followed by ethanol precipitation or evaporation of the solvent would provide a highly purified source of modified RNA.

EXAMPLE 3

Differential Interaction with Immobilized Hydrocarbon Chains

Direct interaction between RNA molecules bearing hydrophobic groups and hydrophobic groups attached to a solid support would provide an efficient means to separate RNA from contaminants. Hydrophobic solid supports include ethyl-, propyl-, butyl-, pentyl-, hexyl-, octyl-, decyl and dodecyl-agarose affinity chromatography media (Catalogue ref. AAF-8, Sigma-Aldrich Chemicals). Interaction between the modified RNA and the media should be stronger with longer chain lengths attached to either the RNA or immobilized support. By careful choice of the binding solution it is possible to selectively bind RNA to the beads whilst the contaminants such as DNA are retained in the binding solution. The polarity of the solvent used for binding and washing, the type and concentration of detergent, temperature of interaction and carbon chain length used will all influence the effectiveness of the purification. 60 μl of ethyl-agarose or dodecyl-agarose beads (Sigma, USA) were washed twice in 200 μl of 1.7M ammonium sulphate and collected by centrifugation at 3000 g for 5 seconds between washes. 40 μl (20%) of the beads in 1.7M ammonium sulphate were added to 300 ng of isatoic anhydride labeled RNA. It was found that the fluorescent isatoic anhydride modification could be used to monitor binding to the hydrophobic beads under ultra-violet light. On addition to the beads, fluorescent RNA moved from the solvent to the beads within a few seconds demonstrating interaction between the modified RNA and the hydrophobic surface. It was also found that the interaction between the modified RNA and dodecyl-agarose was very strong: 1% TWEEN/1% TRITON X-100, 6M urea, 100% ethanol or loading the sample in a well of an agarose electrophoresis gel and subjecting the bead-RNA complex to 100V for 15 min. failed to displace the labelled RNA from the dodecyl-agarose bead whilst 50 mM sodium phosphate buffer removed most of the modified RNA from ethyl-agarose beads. An intermediate binding affinity between ethyl and dodecyl was found in the ease of releasing modified RNA from propyl, pentyl and octyl-agarose. Overall, the strength of the hydrophobic interaction is proportional to carbon chain length increasing from ethyl, propyl, pentyl, octyl to dodecyl-agarose.

This demonstrates that as expected, the strength of the hydrophobic interaction between modified RNA and the hydrophobic bead is dependent on the chain length and therefore hydrophobicity of the bead. The ease with which modified RNA may be removed from the hydrophobic surface is therefore a function of the hydrophobicity of both the modification at the 2' position of the RNA and the nature of the hydrophobic surface. Preferred chain lengths are octyl and longer. Binding was found to take approximately 2 minutes and took place even in low salt binding buffers such as 50 mM sodium phosphate buffer, pH 7.2 or water, although with water the amount of binding is reduced compared with 1.7M ammonium sulphate. It will be apparent that RNA can be separated from other cellular components based on an initial modification reaction of the 2'-OH groups followed by selective hydrophobic binding to a hydrophobic surface, and where necessary subsequent release before use for hybridisation etc. This approach could be useful for purifying RNA from biological samples such as cells for gene expression studies or viral RNA from biological material such as body fluids such as serum and cerebral spinal fluid.

Release of the modified RNA from the solid support is effectuated by the addition of;

1) a deprotecting agent such as alkali, ammonia or KCN that leads to acyl cleavage and therefore separation of the RNA from the hydrophobic groups, 2) use of a solvent with a low polarity such as pentane or toluene that will preferentially bind to the hydrocarbon side chains of the RNA and thereby disrupt the hydrophobic interaction with the solid support, or 3) a detergent such as SDS or TWEEN that is capable of disrupting the hydrophobic interaction with the solid support.

4) addition of a Lewis acid such as $MnCl_2$ to cleave methoxyethoxymethyl ethers at the 2'-OH position, thus releasing the RNA from the hydrophobic surface.

EXAMPLE 4

Immobilization on BCPB Beads with Subsequent Secondary Modification Reaction 2 mg of BCPB beads were added to 40 µl of THF and then 512 ng of BMV RNA (Promega, US) in 2 µl of water was added and briefly vortexed then incubated for 10 min at 22° C. 1 µl (10 pmol) of acetic anhydride was then added in 20 µl of THF containing 180 µg of DMAP. The reaction was allowed to proceed for a further 5 min at 22° C. and then stopped with 200 µl of 70% ethanol and the beads collected by centrifugation at 3000 rpm for 5 sec and then washed a second time in 70% ethanol and twice in 200 µl of water before being resuspended in 20 µl of water. The secondary reactant such as acetic anhydride or acetic-formic anhydride could also carry various labels such as 14C or 3H allowing the amount of RNA to be determined using a scintillation measurement of the washed RNA-bead complex. Alternatively, the secondary reactant could be fluorescent such as isatoic or N-methylisatoic anhydrides or carry a label such as biotin permitting quantification of the amount of RNA bound to the bead. The secondary reactant would be expected to modify at least 75% or more of the 2'-OH groups so that the RNA is protected from degradation from for example ribonucleases. However, the secondary modification could also provide a means for a second purification step. For example the secondary reactant could contain a hydrophobic group or a ligand such as biotin for binding to a streptavidin bead. On release from the first solid phase such as BCPB beads the RNA would be specifically bound to a hydrophobic surface such as dodecyl-agarose beads.

EXAMPLE 5

Probe Hybridization to RNA Immobilized on BCPB Beads 100 ng of BMV RNA (Promega, USA) in 1 µl of water was added to 40 µl of either THF or DMSO and then 3 mg of BCPB beads added, mixed and incubated at 22° C. for 15 min, the beads were then washed once in 100 µl of 70% ethanol, once in 100 µl of 10% SDS and three times 100 µl of water. The beads were finally resuspended in 50 µl of Church hybridization buffer (0.5M NaPi pH7.2, 7% SDS and 1 mM EDTA) containing a 32P dCTP radiolabelled probe complementary to the BMV RNA sequence (RNA 2, nucleotides 1–321). Following incubation for 2 hrs at 55° C., the beads were washed twice in 500 µl of 2×SSC/0.1% SDS to remove non-hybridized probe and then the amount of radioactivity remaining on the beads was determined using a scintillation counter.

The probe can be branched or linear and labeled with a radioactive, fluorescent, colored, affinity or protein label in a manner identical to standard hybridization procedures. In this way, the amount of RNA complementary to the probe can be quantitatively determined. This could be useful for example when determining the abundance of transcripts representing specific genes in different tissues. In this case, purified RNA from the tissue of interest could be immobilized onto the BCBP beads and complementary labeled probes hybridized. Unlike a traditional dot blot (Sambrook et al., (1989) Molecular Cloning: A Laboratory Manual, CSH) the RNA is attached to beads and not a membrane, therefore the kinetics of hybridization are improved (see Wilkins Stevens et al. (1999) Nucleic Acids Res. 27:1719). Automation of bead handling could be enhanced by the use of paramagnetic particles. Other uses could include diagnostics where a RNA virus from, for example a body fluid such as serum, is immobilized on the BCPB bead or other solid phase reactant and a probe representing a viral sequence hybridized to the RNA-bead complex. The amount of probe hybridized to the bead would indicate the amount of viral RNA in the starting material.

EXAMPLE 6

Use of Bifunctional Acid Chlorides to Immobilize RNA

To 5 µl of QIAEX silica particles (Qiagen, Germany) in water was added 100 µl of tetrahydrofuran (THF) and the particles washed once by centrifugation and then resuspended in 40 µl of THF containing 15 µl (65 pmol) of sebacoyl chloride and the reaction incubated at 22° C. for 3 hrs. The particles were then washed twice in 100 µl of THF in order to remove unreacted sebacoyl chloride and then resuspended in 20 µl of THF. The sebacoyl chloride at this stage is covalently attached to the silica particles in such a way that there is one unreacted acid chloride group free to react with the RNA which is added to 20 µl of the particles in 1 µl of water. The reaction is allowed to proceed at 22° C. for 30 minutes and then the particles washed with 200 µl of 70% ethanol and twice in 200 µl of water. Non-basic solvents are preferred so that the RNA is not degraded during the course of the reaction. Suitable solvents include THF, dimethyl sulphoxide and dimethyl formamide. Catalysts such as DMAP, 4-pyrrolidinopyridine, other aminopyridine catalysts, tetrabutylammonium fluoride or tributylphosphine may be used in catalytic quantities during the reaction. The covalently immobilized RNA can then be used for a variety of downstream applications such as RT-PCR amplification, hybridization and NASBA,

EXAMPLE 7

Purification of Acylated RNA Using a PVDF Membrane

The following method was used. A radioactively labeled RNA transcript was produced using a RIBOPROBE kit (Promega, USA), T3 RNA polymerase, $^{32}P$ UTP and a plasmid DNA template (pGEMEX-1 linearized with Hind III). Approximately 10,000 cpm of radiolabelled RNA (10 ng) was modified in separate reactions with acetic formic anhydride, acetic anhydride, propionic anhydride or butyric anhydride as follows.

Formylation: 5 µl of acetic formic anhydride was added to a 100 µl reaction containing 95 µl THF, 16 mg (195 µmol) 1-methylimidazole, and 10 ng radiolabelled RNA and the reaction incubated at 22° C. for 10 min before purification by ethanol precipitation.

Figure 1:
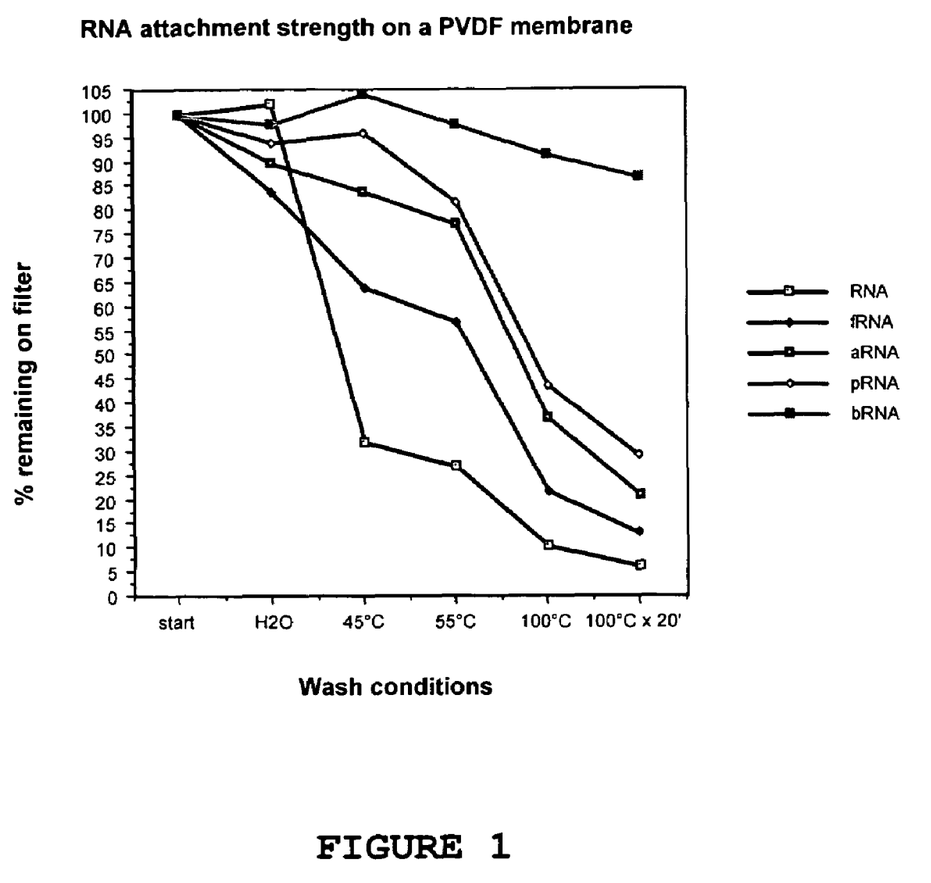
FIG. 1 shows RNA attachment strength on a PVDF membrane, plotting the % of remaining RNA on filter against wash conditions.

Acetylation, propanoylation, butanoylation: A 20 µl reaction containing 19 µl triethylamine, 100 µg DMAP, 2 µl of anhydride and 10 ng of radiolabelled RNA was mixed and incubated for 1 hr at 22° C. All modified RNA samples were purified by ethanol precipitation. Approximately equal amounts of RNA or modified RNA (5,000 cpm) was spotted onto a hydrophobic PVDF membrane (Amersham Pharmacia, UK) that had been pre-wet with methanol. After briefly air drying the membrane, the radioactivity in each spot was measured before and after the following wash treatments, water 5 min at 22° C., water 5 min at 45° C., water 5 min at 55° C., 0.1% SDS 5 min at 100° C., 0.1% SDS 20 min at 100° C. The amount of radioactivity remaining in each spot was quantitated using an Instant Imager (Hewlett Packard). The results are presented graphically in FIG. 1. It is apparent that the butanoylated RNA had the greatest capacity to be retained on the membrane as the following percentage of sample remaining after 20 min of boiling 0.1% SDS show. RNA 6.5%, formyl RNA 13%, acetyl RNA 21%, propanoyl 29% and butanoyl 89%. Although there is a clear linear increase in the percentage of sample retained as the modification at the 2'-OH group increases in size from formyl to propanoyl, there is a much larger retention of sample with butanoylated RNA. In summary, over 93% of the RNA sample is lost whilst only 11% of the butanoylated RNA sample is lost after 20 min of boiling. Binding of modified RNA to hydrophobic surfaces such as PVDF membranes or polystyrene beads is therefore a simple and realistic means to purify it from less hydrophobic contaminants such as DNA or carbohydrates. This may prove useful for purifying RNA from biological samples such as blood or tissue samples for use in a diagnostic test.

EXAMPLE 8

Binding of RNA to Silica Particles

Approximately 5,000 cpm of a 75 nucleotide RIBO-PROBE radiolabelled (Promega, USA) RNA, formyl RNA (fRNA), acetyl RNA (aRNA), propanoyl and butanoyl RNA (pRNA and bRNA) was mixed with 10 µl of silica (QIAEX™) particles as described (Qiagen, Germany) and then washed two times in 0.5 ml of buffer PE. The pellet was allowed to briefly air dry before adding 20 µl of water and incubating for 5 min at 22° C. After the water was removed, the amount of cpm remaining on the beads was measured and the results are shown graphically in FIG. 2.

Figure 2:
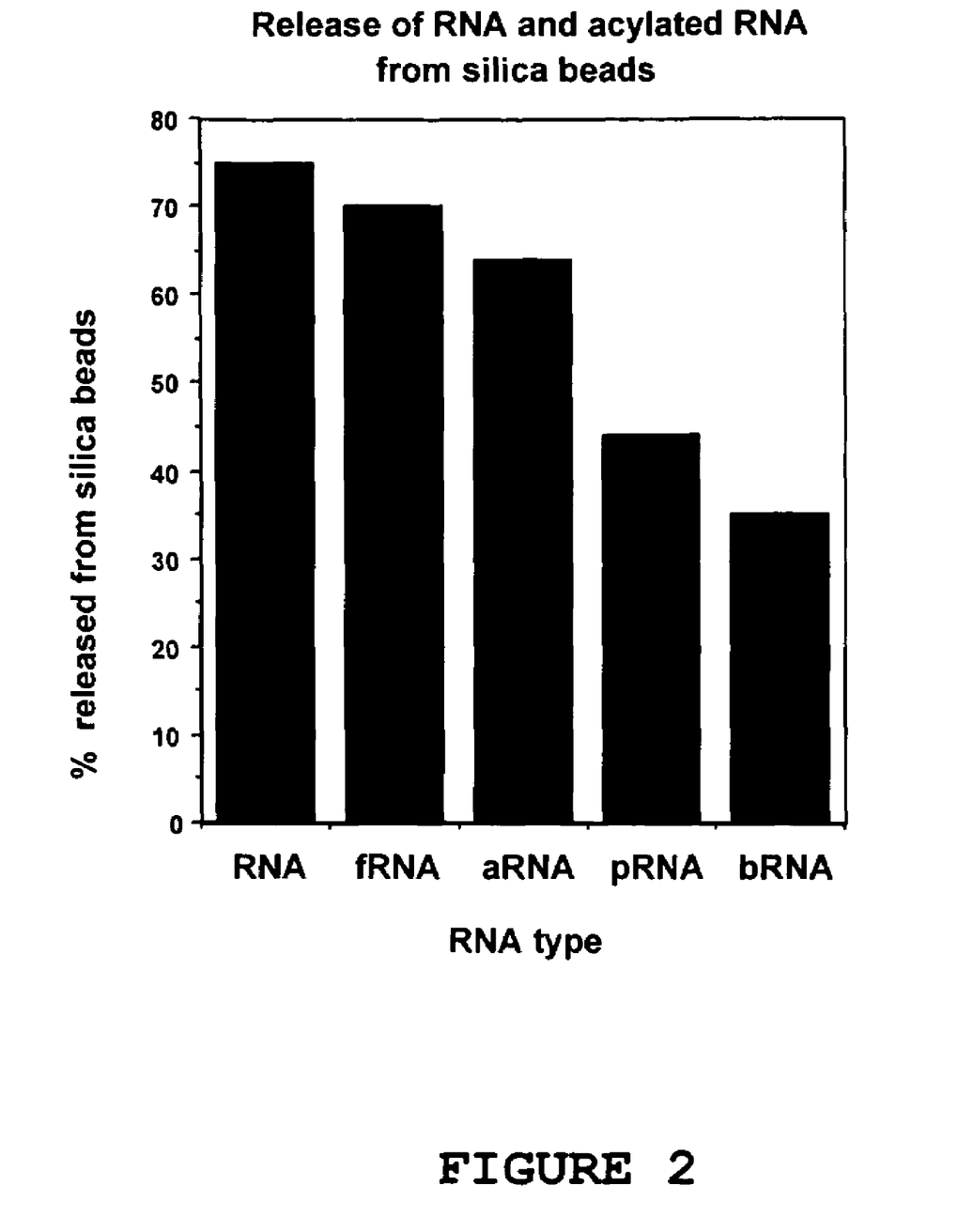
FIG. 2 shows data relating to the release of RNA and acylated RNA from silica beads, plotting the % RNA released from silica beads against RNA type.

There was a proportional relationship between the length of the modifying group on the 2'-OH group and the retention on the bead. Although 75% of the RNA was released from the beads, less than half the amount of the butanoylated RNA was released suggesting it is possible to purify modified RNA on the basis of the size of the modification. It was found that with longer incubation periods at 50° C. in 10 mM Tris-HCl (pH 7) it was possible to release over half (54%) of the butanoylated RNA from the silica beads.

EXAMPLE 9

Modification of RNA Whilst Still Bound to Silica Beads

The modification was carried out as follows. 1 µg of 0.24–9.4 kb RNA ladder (Life Technologies) was mixed with 4 µl of silica beads (QIAEX, Qiagen, Germany), mixed with 12 µl of saturated sodium iodide and incubated for 5 min at 22° C. The sodium iodide was removed and the washed beads added to 19 µl of triethylamine, 100 µg of DMAP and 2 µl of acetic anhydride and the reaction incubated for 5 min at 22° C. The beads were then washed two times in 500 µl PE buffer A and centrifuged for 5 min at 13,000 rpm. The RNA was eluted in 5 µl of water and analysed by agarose gel electrophoresis. Compared with an identical RNA modification reaction with no acetic anhydride added, the modified RNA was substantially intact and migrated identically to a acetylated RNA modified by the standard procedure. Acetylation of RNA can therefore occur whilst the RNA is bound or attached to a solid support or surface. This potentially offers advantages when high throughput of samples is required or when RNA is purified using silica beads for example for diagnostic purposes from blood.

EXAMPLE 10

Purification of Modified RNA from the Reaction Components Using Silica Beads

In order to purify the modified RNA from the reaction components the following procedure was used. A standard 20 µl modification reaction containing 19 µl triethylamine, 100 µg of DMAP, 2 µl of acetic anhydride and 1 µg of 0.24–9.4 kb RNA ladder (Life Technologies) was incubated for 2 min at 22° C. and quenched by the addition of 20 µl of ethanol. 4 µl of silica particles (QIAEX, Qiagen, Germany) were added and mixed for 5 min at 22° C. The particles were pelleted at 13,000 rpm for 5 min and washed once in 50 µl PE and eluted in 10 µl of 10 mM Tris-HCl (pH 7.5) at 22° C. Recovery of the acetylated RNA was estimated to be over 75%. The novel finding that nucleic acids can bind to silica beads in 95% organic solvent suggests a general means to purify nucleic acids or products thereof from organic reactions or biological samples.

EXAMPLE 11

BCPB Beads RNA Immobilisation Reaction 2 mg of BCPB beads were added to 40 µl of THF and then 512 ng of BMV RNA (Promega, US) in 1 µl of water was added and briefly vortexed then incubated for 10 min at 22° C. The reaction was stopped with 200 µl of 70% ethanol and the beads collected by centrifugation at 3000 rpm for 5 sec and then washed a second time in 70% ethanol and twice in 200 µl of water before being resuspended in 20 µl of water.

RT-PCR:

One half (10 µl) of the RNA-BCPB beads were added to a 20 µl reverse transcription reaction containing the following final component concentrations: 200 mM Tris-HCl (pH 8.4 at 24° C.), 75 mM KCl, 2.5 mM $MgCl_2$, 10 mM DTT, 1 mM dNTP's, 110 ng of BMV-R oligonucleotide primer (GAGCCCCAGCGCACTCGGTC) (SEQ ID NO: 1) and 100 units of the reverse transcriptase MULV Point Mutant (Promega, USA). The reaction was allowed to proceed for 20 min at 42° C. and 10 min at 37° C. The cDNA/RNA BCPB bead complex was then washed four times in 200 µl 100 mM NaCl/10 mM Tris HCl pH7.5, once in 200 µl of water before resuspension in 10 µl of water. The cDNA can then be used directly in a PCR reaction as follows.

The PCR was carried out in a final volume of 25 µl with final concentrations of 15 mM Tris-HCl pH 8.8, 60 mM KCl, 2.5 mM $MgCl_2$, 400 µM each dNTP, 10 pmol of each primer BMV F (CTATCACCAAGATGTCTTCG) (SEQ ID NO: 2) and BMV R (GAGCCCCAGCGCACTCGGTC) (SEQ ID NO: 1) and 1 unit Taq DNA polymerase (Amersham Pharmacia Biotech, UK). 1 µl of the bead complex was added per reaction. Cycle parameters were 94° C.×20 sec, 55° C.×20 sec and 72° C.×30 sec for 31 cycles. PCR products were visualized following agarose gel electrophoresis and staining with EtBr. Excellent amplification of a 150 bp BMV sequence was obtained using this method with product yields similar to the same amount of RNA free in solution.

EXAMPLE 12

RNase Treatment of BCPB-RNA

A large part of the RNA bound to BCPB can be cleaved using ribonucleases such as ribonuclease ONE™ (Promega, US) and RNases A. A BCPB-radioactive RNA (RIBO-PROBE, Promega, USA) complex was mixed in a 20 µl reaction containing 1× RNase ONE buffer (Promega, USA) and 1 ng of enzyme for 30 min at 37° C. and the amount of radioactivity released was counted using a scintillation counter. Using either RNase A or RNase ONE, 64–68% of the RNA was cleaved demonstrating that the RNA is attached to the BCPB bead in a conformation suitable for enzyme recognition. An identical reaction with DNase I resulted in less than 5% RNA release.

EXAMPLE 13

Purification of RNA from a Solution Containing BSA

Serum albumin is a major component of blood. In order to test the effect of serum albumin (BSA) on RNA binding to BCPB beads, the following experiment was carried out. To 20 ng (1 µl) of $^{32}$P UTP radiolabelled RIBOPROBE RNA (Promega, USA) containing two transcripts of 250 and 1500 nucleotides, was added either 1 µl of water, or 100 ng, 1 µg or 10 µg of acetylated BSA in 1 µl of water and then mixed with 40 µl of THF containing 1 mg of BCPB beads. The four reactions were mixed and incubated at 22° C. for 3 min, the beads washed with 100 µl of 70% ethanol and then with 50 µl of 20% SDS. The overall percentage of captured RNA was similar for all three of the reactions containing BSA (22–24%) compared with 46% for the reaction containing no protein. This demonstrates that although the amount of RNA captured is reduced by half in the presence of protein, high protein concentrations (5 µg/µl) are compatible with BCPB bead purification.

EXAMPLE 14

Pre-Reaction of the Protein Component with Acid Chloride

In order to reduce non-specific binding of protein to the BCPB beads, the protein/RNA mixture was first reacted with acetyl chloride. To 40 µl of DMSO containing 1 µl of 6M sodium perchlorate, 1 µl of water, 1 µl of serum and 1 µl (20 ng) of radiolabelled RNA was added 1 µl of acetyl chloride solution, mixed and incubated at 22° C. for 5 minutes before the addition of 3 mg BCPB beads. RNA binding efficiency compared with a parallel reaction with no acetyl chloride in two separate experiments indicated that 4.2 and 5.4 times more RNA bound to the beads when the serum had been pre-acetylated. This enhancement of RNA binding may be the result of amino-acids and carbohydrates in the serum becoming acetylated and therefore not competing with the 2'-OH groups of the RNA for the BCPB beads.

EXAMPLE 15

RT-PCR Amplification of RNA Purified from Serum 10 ng of BMV RNA (Promega, USA) in 1 µl of water was added to 1 µl of fresh human serum and then mixed with 40 µl of either THF or DMSO in the presence or absence of 150 mM sodium perchlorate or 0.5% SDS (final concentrations) and then 3 mg of BCPB beads added, mixed and incubated at 22° C. for 16 min, the beads were then washed once in 100 µl of 70% ethanol, once in 100 µl of 10% SDS and three times 100 µl of water. The beads were finally resuspended in 8 µl of water before addition to the RT reaction.

One half (4 µl) of the RNA-BCPB beads were added to a 20 µl reverse transcription reaction containing the following final component concentrations: 200 mM Tris-HCl (pH 8.4 at 24° C.), 75 mM KCl, 2.5 mM MgCl$_2$, 10 mM DTT, 1 mM dNTP's, 110 ng of BMV-R oligonucleotide primer (GAGC-CCCAGCGCACTCGGTC) (SEQ ID NO: 1) and 100 units of MULV Point Mutant (Promega, USA). The reaction was allowed to proceed for 40 min at 42° C. The cDNA was then used directly in a PCR reaction as follows.

The PCR was carried out in a final volume of 25 µl with final concentrations of 15 mM Tris-HCl pH 8.8, 60 mM KCl, 2.5 mM MgCl$_2$, 400 µM each dNTP, 10 pmol of each primer BMV F (CTATCACCAAGATGTCTTCG) (SEQ ID NO: 2) and BMV R (GAGCCCCAGCGCACTCGGTC) (SEQ ID NO: 1) and 1 unit Taq DNA polymerase (Amersham Pharmacia Biotech, UK). 2 µl of the bead complex/cDNA reaction was added per reaction. Cycle parameters were 94° C.×10 sec, 55° C.×10 sec and 72° C.×15 sec for 30 cycles. PCR products were visualized following agarose gel electrophoresis and staining with EtBr. It was found that none of the reactions in THF led to an amplification product even if sodium perchlorate or SDS had been added. However, all the DMSO reactions provided a suitable template for RT-PCR, with the addition of 150 mM sodium perchlorate or 0.5 mM SDS (final concentrations) increasing the amount of PCR product by 4.3 and 11 times respectively. Other successful RT-PCR reactions were obtained from 100 ng BMV RNA templates purified from 1 µl of serum using 10 µl of DMSO and 3 mg BCPB beads containing 15 or 150 mM sodium perchlorate, or 2% SDS, or 400 mM guanidine thiocyanate or 600 mM urea. BCPB beads are therefore useful to purify RNA for RT-PCR analysis from serum.

The invention claimed is:

1. A method of isolating RNA from a biological sample of a human or animal subject comprising an oligo- or polynucleotide from a sample comprising the steps of:
   (a) treating the sample with a reactant capable of covalently modifying the 2'-OH position of the ribose rings of the RNA under conditions so that a proportion of the 2'-OH positions of the ribose rings bear a substituent; and
   (b) preparing isolated RNA therefrom by separating material containing the substituent from the sample on the basis of a property of the substituent.

2. The method according to claim 1, wherein:
   (a) the step of claim 1 (a) is carried out in a reaction medium which comprises an organic solvent, and optionally wherein said organic solvent comprises an organic base, and further optionally wherein said reactant comprises an acid anhydride, an acid chloride, a carboxylic acid or an N-acylimidazole, and further optionally wherein said reaction medium further comprises an acylation catalyst, and further optionally wherein said the reaction medium further comprises water;
   (b) said RNA comprises mRNA, rRNA or viral RNA;
   (c) said sample comprises a sample from a biological source;
   (d) said sample includes DNA;
   (e) said substituent comprises a solid phase, and optionally wherein said solid phase comprises benzoyl chloride polymer bound (BCPB) beads, silica particles or particles of a glass, and further optionally wherein said solid phase is modified to introduce a reactive group which reactive group is capable of reacting with RNA to capture the RNA on the solid phase, and further optionally wherein said reactive group is introduced by modifying the solid phase with a bi-functional acid halide;
   (f) said substituent comprises a hydrophobic substituent, and optionally wherein said hydrophobic substituent comprises a substituent, OR, wherein R is selected from the group consisting of: $C_1$–$C_{36}$ alkyl; $C_1$–$C_{36}$ alkenyl; $C_1$–$C_{36}$ alkynyl; $C_1$–$C_{36}$ haloalkyl; $C_1$–$C_{36}$ aminoalkyl; $C_1$–$C_{36}$ alkoxyalkyl; $C_1$–$C_{36}$ alkylthioalkyl; $C_1$–$C_{36}$ alkoxyalkoxyalkyl; $C_1$–$C_{36}$ haloalkoxyalkyl; $C_1$–$C_{36}$ aminoalkoxyalkyl; $C_6$–$C_{36}$ aryl; $C_6$–$C_{36}$ alkylaryl; $C_6$–$C_{36}$ arylalkyl; $C_6$–$C_{36}$ arylalkenyl; $C_1C_{36}$ alkanoyl; $C_1$–$C_{36}$ alkenoyl; $C_1$–$C_{36}$ haloalkenoyl; $C_1$–$C_{36}$ haloalkanoyl; $C_2$–$C_{36}$ haloformylalkanoyl; $C_1$–$C_{36}$ $C_1$–$C_{36}$ aminoalkanoyl; $C_1$–$C_{36}$ azidoalkanoyl; $C_1$–$C_{36}$ carboxyalkanoyl; $C_1$–$C_{36}$ carboxyalkenoyl; $C_1$–$C_{36}$ carboxyalkynoyl; $C_1$–$C_{36}$ alkylaminoarylalkanoyl; $C_1$–$C_{36}$ alkoxycarbonyl; $C_1$–$C_{36}$ alkenyloxycarbonyl; $C_1$–$C_{36}$ alkylsulfonyl; $C_6$–$C_{36}$ arylanoyl; $C_6$–$C_{36}$ arylalkenoyl; $C_6$–$C_{36}$ aryloxyalkanoyl; $C_6$–$C_{36}$ alkylarylalkanoyl; $C_6$–$C_{36}$ haloarylalkanoyl; $C_6$–$C_{36}$ aminoarylalkanoyl; $C_1$–$C_{36}$ alkylsilanyl; $C_1$–$C_{36}$ trialkylsilanyl and $C_{12}$–$C_{28}$ diarylphosphano; or a substituent R', wherein R' comprises $C_1$–$C_{36}$ alkyl; $C_1$–$C_{36}$ alkenyl; $C_1$–$C_{36}$ alkynyl; $C_1$–$C_{36}$ haloalkyl; $C_1$–$C_{36}$ aminoalkyl; halo; amino; $C_1$–$C_{36}$ alkylamino; $C_6$–$C_{36}$ aryl; $C_1$–$C_{36}$ alkylaryl or $C_1$–$C_{36}$ arylalkyl;
   (g) said hydrophobic substituent of (f) comprises a $C_4$ to $C_7$ carbon chain or ring;
   (h) wherein said reactant comprises butyric anhydride, pentanoic anhydride, hexanoic anhydride or benzoic anhydride;
   (i) said proportion of 2'-OH positions bearing the substituent is at least 10%;
   (j) said hydrophobic substituent of (f) comprises a $C_8$–$C_{12}$ carbon chain or ring, and optionally wherein said proportion of 2'-OH positions bearing the substituent is in the range 1 to 10%;
   (k) said hydrophobic substituent of (f) comprises a $C_{12}$–$C_{36}$ carbon chain or ring, and optionally wherein said proportion of 2'-OH positions bearing the substituent is up to 1%;
   (l) said step (b) comprises contacting the treated sample from step (a) with a hydrophobic solid phase so as to bind the material containing the hydrophobic substituent and optionally washing the material bound to the solid phase, and optionally wherein said hydrophobic solid phase comprises hydrophobic particles, and further optionally wherein said method further comprises a step of eluting the material bound to the hydrophobic solid phase by treating with a detergent, a chaotrope or a solvent, by lowering the salt concentration or by cleaving the substituent from the 2'-OH position of the ribose rings;
   (m) said step (b) comprises the further step of treating the treated sample from step (a) with a lyotrophic salt to aggregate the material containing the hydrophobic substituent as an RNA precipitate, and isolating the precipitate, and optionally wherein said lyotrophic salt comprises ammonium sulphate, an alkali metal chloride, magnesium chloride or calcium chloride; or
   (n) said step (b) comprises treating the treated sample with a non-polar solvent to form a hydrophobic liquid phase which contains the material containing the hydrophobic substituent, and isolating the hydrophobic liquid phase, and optionally wherein said non-polar solvent comprises pentane, cyclohexane, toluene, benzene, light petroleum, xylene or hexane.

3. A preparative method for isolating RNA comprising an oligo- or polynucleotide from a biological sample of a human or animal subject, which method comprises:
(a) collecting a biological sample of blood, cells, tissue or body fluids containing RNA;
(b) treating the sample with a reactant capable of covalently modifying the 2'-OH position of the ribose rings of the RNA under conditions so that a proportion of the 2'-OH positions of the ribose rings bear a substituent; and
(c) isolating the RNA that has been modified at the 2'-OH position from the sample.

* * * * *

UNITED STATES PATENT AND TRADEMARK OFFICE
CERTIFICATE OF CORRECTION

PATENT NO. : 7,244,568 B2
APPLICATION NO. : 10/820423
DATED : July 17, 2007
INVENTOR(S) : Andrew S. Goldsborough It is certified that error appears in the above-identified patent and that said Letters Patent is hereby corrected as shown below:

Item (74):
Title page, "Saliwanchik, Lloys & Saliwanchik" should read
--Saliwanchik, Lloyd & Saliwanchik--.

Column 2,
Line 64, "(Nordhoffet al." should read --(Nordhoff et al.--.

Column 3,
Line 9, "(Potieret al." should read --(Potier et al.--.

Column 5,
Line 61, "2'-OII" should read --2'-OH--.

Column 9,
Lines 25-27, "2'-OH<formyl(—C(O)H)<acetyl(—(O)CH$_3$)<propanoyl (—(—C(O)CH$_2$CH$_3$)<butanoyl(—C(O)CH$_2$CH$_2$CH$_3$)" should read --2'-OH < formyl (—C(O)H) < acetyl (—C(O)CH$_3$) < propanoyl (—C(O)CH$_2$CH$_3$) < butanoyl (—C(O)CH$_2$CH$_2$CH$_3$)--.

Column 14,
Line 61, "TIIF" should read --THF--.

Column 21,
Line 12, "(10 pmol)" should read --(10 µmol)--.

Column 22,
Line 17, "(65 pmol)" should read --(65 µmol)--.

UNITED STATES PATENT AND TRADEMARK OFFICE
CERTIFICATE OF CORRECTION

PATENT NO. : 7,244,568 B2
APPLICATION NO. : 10/820423
DATED : July 17, 2007
INVENTOR(S) : Andrew S. Goldsborough It is certified that error appears in the above-identified patent and that said Letters Patent is hereby corrected as shown below:

Column 27,
Line 63, "$C_1$-$C_{36}$ $C_1$-$C_{36}$ aminoalkanoyl" should read -- $C_1$-$C_{36}$ aminoalkanoyl--.

Signed and Sealed this

Thirtieth Day of October, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Brome Mosaic Virus (BMV)
<220> FEATURE:
<221> NAME/KEY: primer_bind
<222> LOCATION: (1)..(20)

<400> SEQUENCE: 1 gagcccagc gcactcggtc                    20

```
<210> SEQ ID NO 2
<211> LENGTH: 20
<212> TYPE: DNA
<213> ORGANISM: Brome Mosaic Virus
<220> FEATURE:
<221> NAME/KEY: primer_bind
<222> LOCATION: (1)..(20)

<400> SEQUENCE: 2
ctatcaccaa gatgtcttcg                                              20
```